United States Patent [19]

Wang et al.

[11] Patent Number: 4,547,281
[45] Date of Patent: Oct. 15, 1985

[54] GAS ANALYSIS APPARATUS

[75] Inventors: Da Y. Wang, Lexington; Daniel T. Kennedy, Burlington, both of Mass.

[73] Assignee: GTE Laboratories Incorporated, Waltham, Mass.

[21] Appl. No.: 729,892

[22] Filed: May 2, 1985

Related U.S. Application Data

[63] Continuation of Ser. No. 553,856, Nov. 21, 1983, abandoned.

[51] Int. Cl.⁴ ............................................. G01N 27/46
[52] U.S. Cl. ................................... 204/424; 204/1 T; 204/425; 204/426; 204/427; 427/123; 427/126.2; 427/209; 427/226; 427/404; 427/419.1; 427/429
[58] Field of Search ...................... 204/1 S, 421–429; 427/123, 126.2, 209, 226, 404, 419.1, 429

[56] References Cited

U.S. PATENT DOCUMENTS

| | | | |
|---|---|---|---|
| 3,514,377 | 5/1970 | Spacil et al. | 204/1 S |
| 3,691,023 | 9/1972 | Ruka et al. | 204/425 |
| 3,907,657 | 9/1975 | Hzijne et al. | 204/1 S |
| 4,021,326 | 5/1977 | Pollner et al. | 204/429 |
| 4,128,458 | 12/1978 | Obiaya | 204/1 S |
| 4,158,166 | 6/1979 | Isenberg | 204/426 |
| 4,304,652 | 12/1981 | Chiba et al. | 204/426 |
| 4,345,985 | 8/1982 | Tohda et al. | 204/192 |
| 4,381,224 | 4/1983 | Fate et al. | 204/1 S |
| 4,384,935 | 5/1983 | De Jong | 204/426 |
| 4,389,881 | 6/1983 | Butler | 73/116 |
| 4,391,691 | 7/1983 | Linder et al. | 204/408 |

FOREIGN PATENT DOCUMENTS

| | | | |
|---|---|---|---|
| 48-68439 | 9/1973 | Japan . | |
| 56-41939 | 10/1981 | Japan | 204/424 |

OTHER PUBLICATIONS

Takahashi et al., *Mat. Res. Bull.*, vol. 13, pp. 1447–1453 (1978).
Verkerk et al., *J. of Applied Electrochemistry*, vol. 10, (1980), pp. 81–90.
"Oxygen Sensing by Electrochemical Pumping", *Appl. Phys. Lett.* 38(5), Mar. 1, 1981 by Hetrick et al., pp. 390–392.
"Internal-Reference Solid-Electrolyte Oxygen Sensor", *Analytical Chemistry*, vol. 19, No. 12, Oct. 1977 by Haaland, pp. 1813–1817.

*Primary Examiner*—T. Tung
*Attorney, Agent, or Firm*—Hamilton, Brook, Smith & Reynolds

[57] ABSTRACT

A gas concentration sensing or pumping device is formed of a body of solid electrolyte material which exhibits ionic conduction when the concentration of gas is different between first and second surfaces of the body, or which, upon application of a voltage across the body, will cause gas on one side of the body to be pumped to the other side. A thin film of a composition comprising an element selected from the group consisting of rare earth elements, alkaline earth metals, Ga Pb, In, Sn, Ti, Mo and W wherein Bi is the predominant element is formed on a major surface of the body to enhance conductivity at the electrode/body interface. Conductive electrode layers are formed over the film and an opposing major surface. The conductive layers may be formed of porous $LaCrO_3$ and the body may be formed of $ZrO_2$, $CeO_2$ or $ThO_2$. An apertured disc or a layer of gas permeable material is formed over the sensor. A voltage is applied across the body of solid electrolyte causing transport of oxygen through the aperture or pores. The output current measures the oxygen concentration passing therethrough.

18 Claims, 5 Drawing Figures

GAS ANALYSIS APPARATUS

This is a continuation of U.S. patent application Ser. No. 553,856 filed Nov. 21, 1983 now abandoned.

OXYGEN ANALYSIS APPARATUS

1. Technical Field

The technical field of this invention is gas sensing and, in particular, sensing the concentration of oxygen in a volume.

2. BACKGROUND ART

Electrolyte gas sensors and, in particular, solid electrolyte oxygen gas sensors have found wide application in gas monitoring, combustion control, metallurgy, petrology, chemical kenetics and thermodynamic studies. Such sensors generally comprise galvanic cells constructed with stabilized zirconia electrolytes. The conductivity of stabilized zirconia has been shown to be due almost exclusively to oxygen ion transport. therefore, the open circuit emf (E) generated by an oxygen concentration cell using stabillized zirconia electrolyte may be shown to be dependent on the ratio of the oxygen partial pressures on either side of the electrolyte. Thus, if the pressure on one side is a known established reference pressure, the pressure on the other side may be determined by solving the Nernst equation for E (emf):

$$E = \frac{RT}{4F} \ln \frac{P_{O_2}''}{P_{O_2}'} \qquad \text{Equation 1}$$

where R is the gas constant, T is the absolute temperature, F is the Faraday constant, and $P_{O_2}''$ and $P_{O_2}'$ are the oxygen partial pressures on either side of the electrolyte.

D. M. Haaland, in a paper entitled "Internal-Reference Solid-Electrolyte Oxygen Sensor" *Analytical Chem.*, Vol. 49, No. 12, 1977, pp. 1815–1816, describes an oxygen sensor constructed of two cells of stabilized zirconia sealed into a unit using a high temperature platinum zirconia seal. One electrolyte chemical cell monitors the ratio of oxygen partial pressures inside and outside the sensor, while the other solid-electrolyte cell is used for quantitative electro-chemical pumping of oxygen. The internal oxygen reference is generated by initially pumping all oxygen out of the known internal volume of the sensor and then quantitatively pumping oxygen back in until oxygen partial pressures are equal inside and out. This information is used with the above referenced Nernst equation to calculate oxygen partial pressures.

Another technique is shown in U.S. Pat. No. 3,907,657 to Heijne et al. dated Sept. 23, 1975. In this technique a space of known volume is brought to the concentration level to be measured via a connecting means having a high transfer resistance, after which the oxygen is rapidly removed from the space by means of a partition forming part of a wall section of the space in which ionic conduction takes place. The required charge, which is applied to the partition to remove the oxygen, is a measure of the concentration and is used to determine the concentration.

Hetrick et al., in a paper entitled "Oyxgen Sensing by Electro-chemical Pumping", *Appl. Phys. Letter* 38 (5), Mar. 1, 1981, pp. 390–391 describes an oxygen sensor comprising two electro-chemical cells in the form of thin disks of doped zirconium oxide, $ZrO_2$, separated by a hollow ceramic spacer defining an enclosed volume. One cell is the pump and the other is the sensor. A gas aperture is made either on the spacer or on the cells. Between the sensor and the pump, a feedback amplifier is supplied. The amplifier keeps the concentration of oxygen at a constant level by pumping out the extra oxygen molecules. The pumping circuit current is a measure of the concentration to be determined.

The foregoing prior art techniques all suffer from the disadvantage that complex electronic circuits are required to control and execute the measurement. These circuit include charge measuring circuits, current source circuits, and feedback amplifiers. This added complexity is a source of increased cost and lowered reliability.

SUMMARY OF THE INVENTION

This invention comprises a method and apparatus for sensing the concentration of a gas and, in particular, a gas such as oxygen. The apparatus comprises at least one sensor disk of electrolyte material, preferably formed of a powder of stabilized zirconia oxide. This disk acts as as gas sensor and is provided with electrodes on each side of the disk. An apertured disk or alternatively, a layer of gas permeable material is formed on the electrolytic disk.

A voltage divider circuit provides a voltage to the electrode on the sensor disk exposed to the interior volume. An output lead is coupled between the remaining electrode of the sensor disk and a resistive path to ground completes the circuit.

The transport rate of gas through the aperture on the disk, or the pores in the permeable material is linearly proportional to the gas concentration. The dimensions of the aperture or the pores in permeable material influences the transport rate.

In operation, a voltage is applied across the sensor electrodes causing ionic conduction and transport of gas through the apertures or pores. The size of the aperture/pores is chosen such that the current at the output lead is clamped or limited over a wide range of voltage. This limiting current is used to measure the oxygen concentration passing through the aperture/pores. The fact that it is relatively insensitive to applied voltage greatly simplifies the design of the system; which only requires normal power supply voltage and three resistors.

BEST MODE OF CARRYING OUT THE INVENTION

Figure 1:
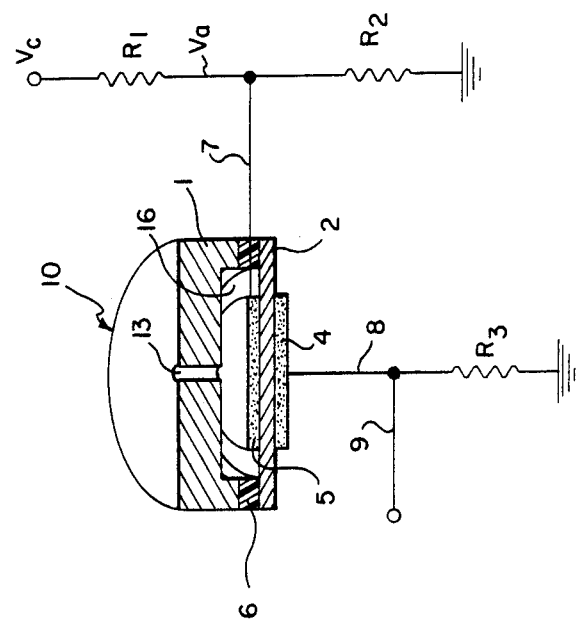
FIG. 1 is a simplified partial perspective view of a first embodiment of the oxygen sensor apparatus of the invention.

A preferred embodiment of this invention can be described in more detail with reference to FIG. 1. FIG. 1 shows a gas sensor and, more particularly, an oxygen gas sensor 10 consisting of a body of electrolyte material formed in the shape of a disk 2. Preferably, this disk is constructed of a sintered powder made up of 85% zirconium oxide ($ZrO_2$) and 15 or 16% by molecular weight of yttrium oxide ($Y_2O_3$). The powder is cold-pressed into a disk and sintered at about 1650° C. for about 4 hours.

Metallic electrodes 4 and 5, preferably of platinum, are painted on both sides of disk 2. Platinum wires 7 and 8 are attached to the electrodes 5 and 4, respectively, and in intimate electrical contact with the electrodes. A second disk 1 of material having a similar coefficient of thermal expansion to that of disk 2, is formed and disposed adjacent disk 2. This second disk is provided with an aperture 13. This second disk may be formed either as an integral part of disk 2 or may be separately formed and hermetically bonded to disk 2 by mans of a glass frit, shown at reference number 6, which extends around the complete periphery of disks 1 and 2.

In a typical example of the invention, disk 1 was made from a powder of $ZrO_2$ and 8% by molecular weight of $Y_2O_3$ and formed in the same fashion as disk 2. The dimensions for this example are as follows: The electrode area of electrodes 4 and 5 were approximately 0.5 cm$^2$. Both disks have the same diameter of approximately 1.1 cm. The aperture diameter in disk 1 is approximately 0.1 mm and the length about 1 mm.

Figure 3:
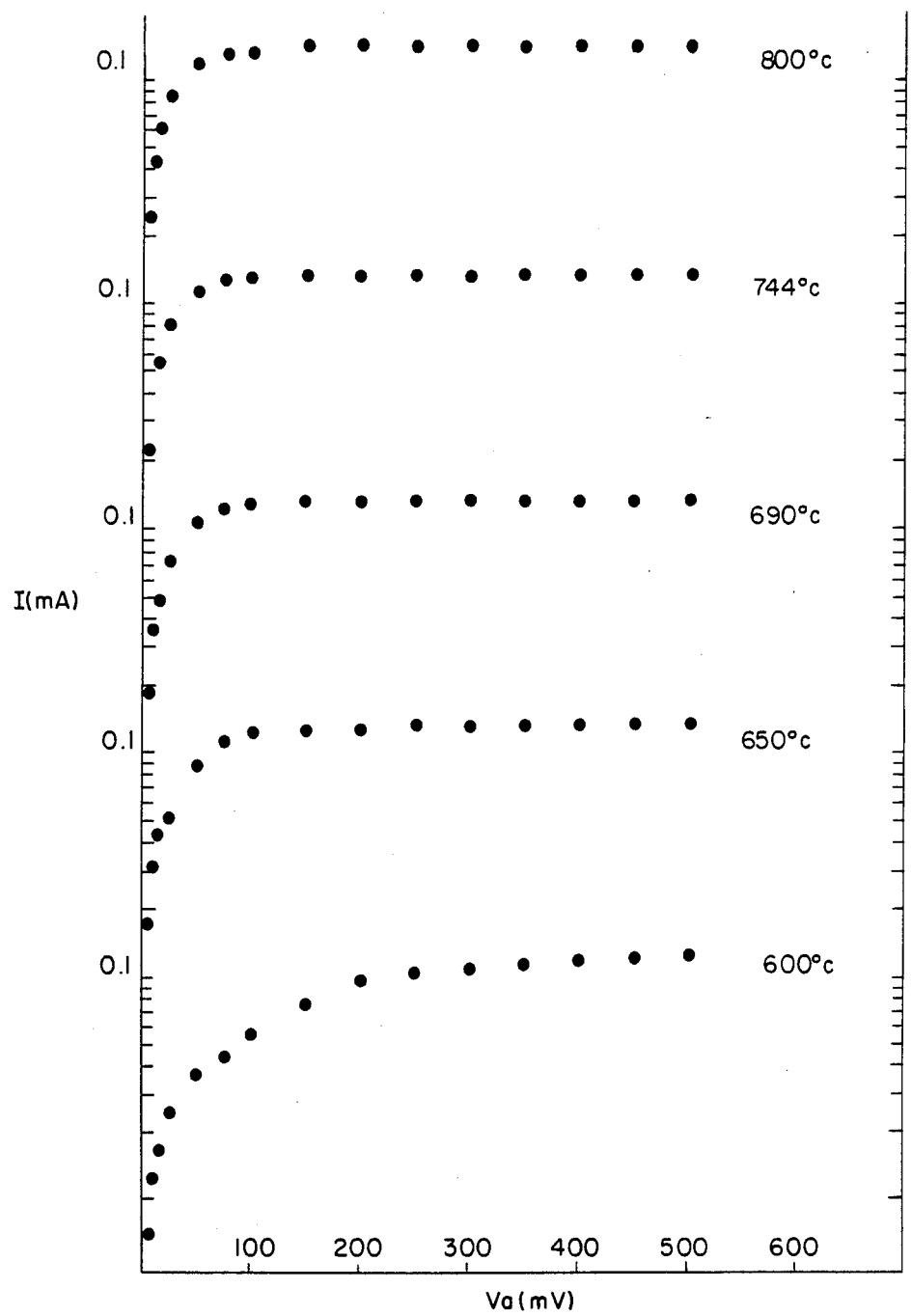
FIG. 3 is a plot of voltage versus current for a specific embodiment of the oxygen sensor apparatus of the invention with measurements taken at different temperature ranges from 600° C. to 800° C. showing the current limiting aspect of the invention.

As shown in FIG. 3, at a temperature of about 650° C. and with a voltage applied ($V_a$) between 100 millivolts and 600 millivolts, a 0.1 mA current output is obtained from terminal 8 of the apparatus of FIG. 1. The voltage $V_a$ is applied at connector 7 to electrode 5. This voltage is obtained by means of a voltage divider network comprising R1 and R2 in series with the voltage source ($V_c$) and ground. The output lead 9 is connected to lead 8 attached to electrode 4 and taken through resistor R3 to ground to complete the circuit back through the voltage divider circuit to $V_c$.

This 0.1 mA current in the graph of FIG. 3 is a measure of an actual oxygen concentration of about 1%.

In practice, the oxygen sensor 10 would be provided with a heater such that the temperature at which the device is operated would be controlled within a suitable temperature range. In the case of automobilie exhaust temperatures, a preferable value of about 700° C. is used. In laboratory applications, where it is desirable to monitor oxygen content for safety purposes, this temperature range would preferably be in the range of 350° C.

Figure 4:
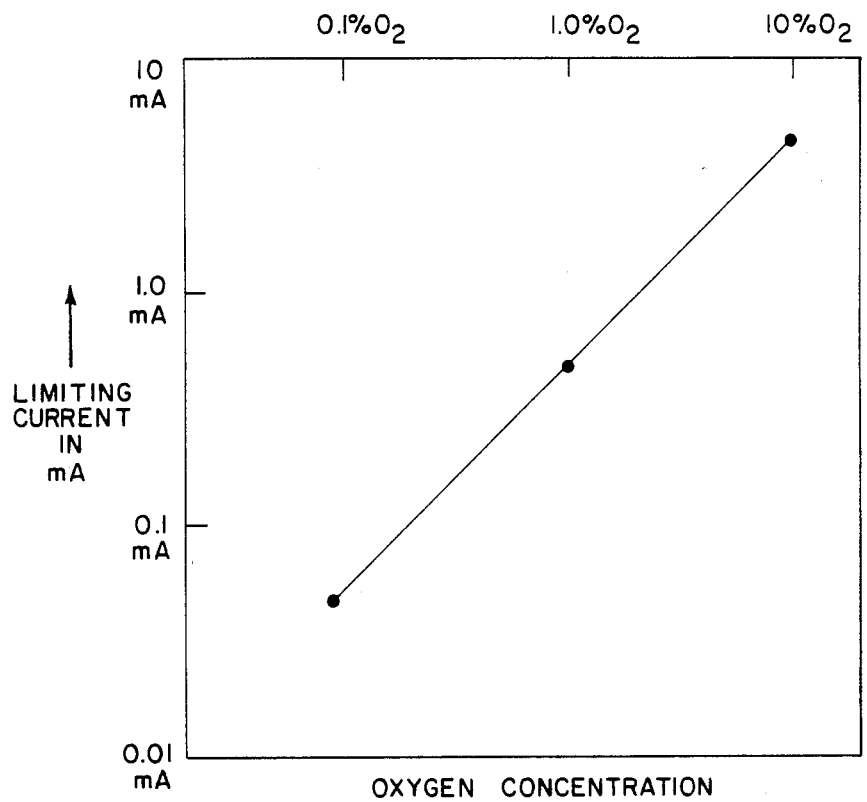
FIG. 4 is a plot of limiting current versus oxygen concentration for an embodiment of the invention.

FIG. 4 shows a plot of limiting current versus corresponding oxygen concentration in a log log scale. The fact that one can obtain a 45° slope in this curve is proof of the linear relationship between the limiting current and the oxygen concentration.

The operation of the device of FIG. 1 may be mathematically explained as follows:

The flux F (number of oxygen molecules/cm$^2$) or rate of flow of a gas, such as oxygen, is equal to:

$$\frac{D}{kT} \frac{\partial P_{O_2}}{\partial x} \qquad \text{Equation 2}$$

where $P_{O_2}$ is equal to the partial pressure of the gas, k is the Boltzmann constant in electron volts per degrees Kelvin, T is the temperature in degrees Kelvin, D is the diffusity in centimeters$^2$ per second and x is the distance in centimeters involved in diffusing the gas.

The relationship between the number of oxygen molecules ($N_v$) in a small volume at a given time (t) is defined by the following equation:

$$\frac{dN_v}{dt} = \frac{-I_p}{4e} = \frac{D}{kT} \frac{P_{O_2}}{\partial x} \qquad \text{Equation 3}$$

The maximum value of the second term on the right side of Equation 3 is $$\frac{D}{kT} \frac{P_{O_2}{}^l}{l}$$

where l is the effective distance the oxygen molecule will have to travel in order to go into the small volume. $P_{O_2}{}^l$ is the ambient gas pressure $P_{O_2}$, the concentration of which is being measured.

As long as a sufficiently high voltage is supplied across the oxygen conducting solid electrolyte, which will give a current larger than the flux F, the oxygen will be pumped out of the small volume. Once steady state is reached, the current ($I_p$) will be defined by the following equation:

$$I_p = \frac{4eD}{kT} \frac{P_{O_2}{}^l}{l} \qquad \text{Equation 4}$$

which shows that the current $I_p$ is directly proportional to $P_{O_2}{}^l$. Analyzing Equation 4, it may be seen that not only is the output current $I_p$ directly proportional to $P_{O_2}{}^l$, but the current change is relatively insensitive to temperature change since:

$$\frac{\Delta I_p}{I_p} = -\frac{\Delta T}{T} + \frac{dD/dt}{D} \Delta T \qquad \text{Equation 5}$$

from which it can be seen that the $\Delta T/T$ term substantially cancels out the second term on the right of the above Equation 5.

Lastly, it may be seen that the stability and accuracy of the voltage is not a significantly important factor, therefore, an inexpensive source of voltage may be utilized.

Figure 2:
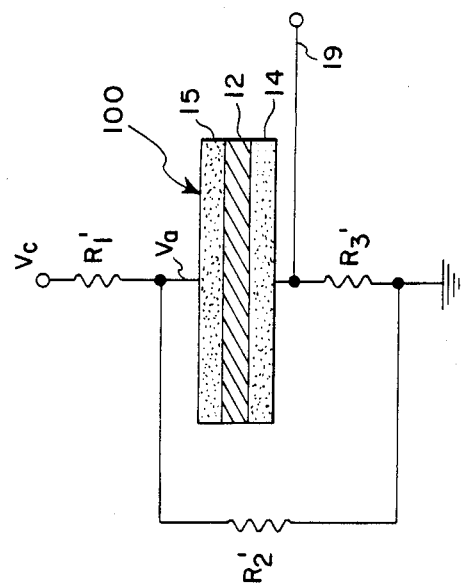
FIG. 2 is a schematic and cross-section view of an alternate embodiment of the oxygen sensor of the invention.

Referring now to FIG. 2, there is shown an alternate embodiment of the invention of much greater simplicity in design than that shown in FIG. 1. The apparatus of FIG. 2 utilizes the same voltage network for a applying voltage V across an electrolyte cell, shown generally at 100. This voltage divider network consists of a voltage source Vc in series with resistor R1' and resistor R2' in series to ground. The voltage $V_a$ from the voltage divider is applied to a porous electrode 15 on cell 100. Electrode 15 is formed in intimate contact with an electrolyte material, such as stabilized zirconia oxide ($ZrO_2$). A similar electrode 14 is applied to the other side of electrolyte 12. However, this electrode 14 is preferably made more porous than the electrode 15, since flow of oxygen is from the exterior surface of electrode 15 through the electrolyte 12 (by ionic conduction) and out to the exterior surface of electrode 14. A lead 19 is provided between resistor R3' and the electrode 14.

A suitable material for the electrodes 14 and 15 would be lanthanum chromate ($LaCrO_3$). The porosity of the top electrode 15 and the bottom electrode 14 may be varied, for example, by mixing graphite with powdered $LaCrO_3$ and using a different grade of graphite for the top electrode 15 than the bottom electrode 14. The graphite is then sintered with the $LaCrO_3$ at about 1650° C. such that the graphite is combusted, leaving pores throughout the $LaCrO_3$ structure. If fine particles are used on the top electrode 15 and larger particles used for the bottom structure 14, the porosity of the top structure 15 will be less than the porosity for the bottom structure.

The advantages of the apparatus of FIG. 2 are that an added step of supplying a separate volume and aperture in the top structure is not required. The small volume for the oxygen gas is effectively supplied by the pores in the electrode 15. Also, there is no requirement for a separate application of electrodes, since the electrodes serve the dual purpose of electrodes and as the aperture or porous means.

In a further alternate embodiment of the invention, the electrode properties of the oxygen sensor are improved. In this embodiment, (hyrated) bismuth nitrate, $Bi(NO_3)_3.5H_2O$ is mixed with (hydrated) yttrium chloride $YCl_3.6H_2O$ in water to form a slurry. The slurry is applied to the top and bottom surfaces of the oxide electrolyte 2 of FIG. 1, such as by brushing. The composite structure is first at about 980° C. for several hours to form a thin film on both surfaces.

Next, the usual metal electrodes, such as Pt, Ag or Au, are formed over the thin films.

Figure 5:
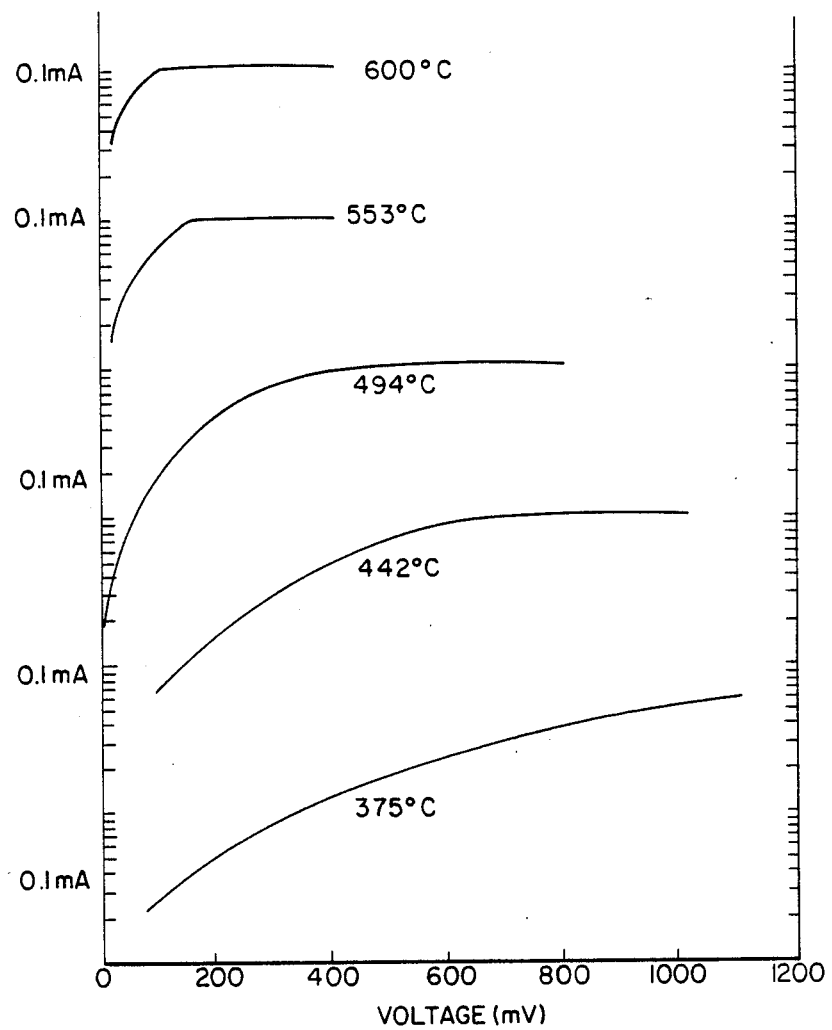
FIG. 5 is a plot of limiting current versus voltage at various temperatures for a further embodiment of the invention.

Applicants have found that the resultant oxygen sensor formed as above recited, has improved limiting current performance at lower temperatures, as may be seen in the graph of FIG. 5, which plots limiting current in milliamps (ma) at different temperature levels versus applied voltage in millivolts (mV). Comparing FIG. 5 (treated surface) with FIG. 3 (untreated surface) it may be seen that for an applied voltage of 200 mV limiting current of 0.1 ma is achieved at 600° C. and 553° C. in the treated sensor, whereas 300 to 400 mV is required in the untreated case.

While the exact reason for this enhanced performance is not known, it is believed that the Y and Bi compounds act as a catalyst to improve conductivity at the electrode/ZrO electrolyte interface. Other rare earth metals, and alkaline earth metals, as well as Ga, Pb, In, Sn, Ti, Mo, or W, may be substituted for the yttrium element. A preferred ratio of Bi to rare earth metal for slurry preparation is about 100 to 60.

There are other equivalents to the embodiments specifically described herein and such equivalents are intended to be covered by the following claims. For example, materials other than $Y_2O_3$, may be used to dope the zirconium oxide ($ZrO_2$) electrolyte. These materials include $Gd_2O_3$ CaO, SnO, MnO, $La_2O_3$, MgO and $Sc_2O_3$. Furthermore, $CeO_2$ or $ThO_2$, may be substituted for the zirconium oxide.

We claim:
1. A gas sensor comprising:
 (a) a sensor body of switch electrolyte material which ionically conducts when the concentration of said gas is different between first and second surfaces of the sensor body;
 (b) a thin film on each said first and second surface of a composition comprising an element selected from the group consisting of rare earth elements, alkaline earth metals, Ga, Pb, In, Sn, Ti, Mo and W and wherein Bi is the predominent element in the composition
 (c) an electrically conductive material formed over the thin film on the first surface of the sensor body; and
 (d) an electrically conductive material formed over the thin film on the second surface of the sensor body.

2. The sensor of claim 1 in which the gas is oxygen and the material of the sensor body comprises material selected from the group consisting of: $ZrO_2$, $CeO_2$ and $ThO_2$.

3. The sensor of claim 2 in which the sensor body material includes a material from the group consisting of $Y_2O_3$, $Gd_2O_3$, CaO, SnO, MnO, $La_2O_3$, MgO, and $Sc_2O_3$.

4. The sensor of claim 1 in which the electrically conductive material comprise porous $LaCrO_3$ and the sensor body comprises material selected from the group consisting of: $ZrO_2$, $CeO_2$ and $ThO_2$.

5. An oxygen gas sensor comprising:
 (a) a sensor body of solid electrolyte material which exhibits ionic conduction in the presence of oxygen gas;
 (b) first and second electrodes permeable to oxygen gas formed over opposite first and second surfaces of said body; and
 (c) said electrodes each comprising a layer of Bi and in a predominant amount an element selected from the group consisting of a rare earth element, an alkaline earth metal, Ga, Pb, In, Sn, Ti, Mo, and W, and a layer of porous $LaCrO_3$.

6. The sensor of claim 5 wherein the layer of porous $LaCrO_3$ is made porous by incorporating particles of carbon of lower combustion temperature into the electrodes as formed and heating the layer to a temperature which combusts the carbon particles having pores in the electrodes.

7. The sensor of claim 6 in which the particles in the first electrode are smaller than the particles in the second electrode.

8. The method of forming a gas sensor comprising the steps of:
 (a) forming a sensor body of solid electrolyte material ionically conductive in response to the concentration of said gas, said body having first and second opposing external surfaces;
 (b) forming a slurry comprising Bi and a rare earth metal on said first and second surfaces of said sensor body to obtain a first and a second film respectively;
 (c) forming a first electrically conductive material on said first film over said first surface of said sensor body;
 (d) forming a second electrically conductive material on said second film over said second surface of said sensor body.

9. A gas sensor made in accordance with the method of claim 8.

10. Apparatus comprising:
 a. a body of solid electrolyte material which ionically conducts in the presence of a gas;

b. a film on a first surface of said body; said film being of a composition comprising an element selected from the group consisting of rare earth elements, alkaline earth metals, Ga, Pb, In, Sn, Ti, Mo and W wherein Bi is the predominant element in the composition;

c. an electrically conductive electrode formed over the film on the first surface of the sensor body; and d. an electrically conductive electrode formed over an opposing second surface of the sensor body.

11. The apparatus of claim 10 in which the gas is oxygen and the material of the body comprises material selected from the group consisting of: $ZrO_2$, $CeO_2$ or $ThO_2$.

12. The apparatus of claim 10 in which the electrodes are formed of porous $LaCrO_3$ and the body comprises material selected from the group consisting of: $ZrO_2$, $CeO_2$, or $ThO_2$.

13. Apparatus comprising:
(a) a body of solid electrolyte material which exhibits ionic conduction in the presence of a gas;
(b) first and second electrodes permeable to said gas formed over opposite first and second surfaces of said body; and
(c) one of said electrodes comprising a composition of Bi in a predominant amount and an element selected from the group consisting of a rare element, an alkaline earth metal, Ga, Pb, In, Sn, Ti, Mo and W, and a conductive element.

14. The apparatus of claim 13 wherein the conductive element is Pt, Ag or Au.

15. The apparatus of claim 13 wherein the conductive element is $LaCrO_3$.

16. Apparatus comprising:
(a) a first body of solid electrolyte material capable of ionic conduction between two major surfaces of the body in the presence of a gas concentration differential between said surfaces and capable of pumping gas from one such surface to the other upon application of a voltage across said surfaces;
(b) electrodes formed over said two surfaces;
(c) one of said electrodes including film means for improving the conductivity of the electrode/body interface formed between said one electrode and one of said surfaces; said film means being a composition comprising Bi in a predominant amount and an element selected from the group consisting of a rare earth element, an alkaline earth metal, Ga, Pb, In, Sn, Ti, Mo and W;
(d) an apertured body disposed in spaced apart adjacent relation to said first body and having a thermal coefficient of expansion similar to said first body; and
(e) bonding means for bonding said apertured body to said first body leaving a small enclosed volume which is hermetically sealed except for said aperture.

17. The apparatus of claim 16 wherein the bonding means comprises glass frit.

18. The apparatus of claim 16 wherein gas is pumped into said volume by applying a voltage across said electrodes.

* * * * *

UNITED STATES PATENT AND TRADEMARK OFFICE
CERTIFICATE OF CORRECTION

PATENT NO. : 4,547,281

DATED : Oct. 15, 1985

INVENTOR(S) : Da Y. Wang and Daniel T. Kennedy

It is certified that error appears in the above—identified patent and that said Letters Patent is hereby corrected as shown below:

Claim 1, line 2, "a sensor body of switch electrolyte material" should read --- A sensor body of solid electrolyte material---.

Claim 6, lines 5-6, "having pores in electrodes" should read ---leaving pores in electrodes---

Signed and Sealed this

Eleventh Day of March 1986

[SEAL]

*Attest:*

DONALD J. QUIGG

*Attesting Officer*  *Commissioner of Patents and Trademarks*